United States Patent [19]

Orr et al.

[11] 4,400,198

[45] Aug. 23, 1983

[54] HERBICIDAL TETRAHYDROFURAN DERIVATIVES

[75] Inventors: Alexander F. Orr; Michael D. Barker, both of Sittingbourne, England

[73] Assignee: Shell Oil Company, Houston, Tex.

[21] Appl. No.: 283,704

[22] Filed: Jul. 16, 1981

Related U.S. Application Data

[63] Continuation-in-part of Ser. No. 225,950, Jan. 19, 1981, abandoned.

[30] Foreign Application Priority Data

Jan. 21, 1980 [GB] United Kingdom ............... 8001921
Dec. 31, 1980 [CA] Canada ................................. 367728
Jan. 19, 1981 [GB] United Kingdom ............... 8101556

[51] Int. Cl.$^3$ ............... C07D 307/12; C07D 405/12; A01N 43/08; A01N 43/40
[52] U.S. Cl. ................................. 71/88; 71/94; 546/270; 546/283; 549/475
[58] Field of Search ............... 546/283, 270; 549/488, 549/475; 71/94, 88

[56] References Cited

U.S. PATENT DOCUMENTS

| Re. 30,574 | 4/1981 | Barker et al. ............... 71/88 |
| 4,116,669 | 9/1978 | Barker et al. ............... 71/88 |
| 4,146,384 | 3/1979 | Schmidt et al. ............ 71/88 |
| 4,289,884 | 9/1981 | Barker ...................... 546/283 |

FOREIGN PATENT DOCUMENTS

| 2 | 12/1978 | European Pat. Off. ............ 71/88 |
| 2724677 | 12/1978 | Fed. Rep. of Germany ........ 71/88 |

Primary Examiner—Alan L. Rotman

[57] ABSTRACT

Compounds of the general formula

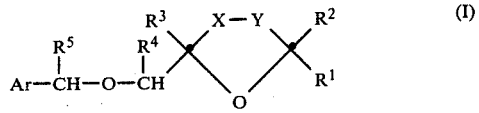

wherein
each of $R^1$ and $R^2$ independently represents a hydrogen atom or an optionally substituted alkyl, cycloalkyl or aryl group, or $R^1$ and $R^2$ together represent an optionally substituted alkylene group;
each of X and Y independently represents one of the groups $CR^6R^7$, $C=O$, $C=N-Z$, $CH-NH_2$

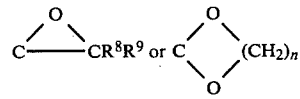

in which
n is 2 or 3;
$R^6$ represents a hydrogen atom, an optionally substituted alkyl or aryl group or a group of formula —OA in which A represents a hydrogen atom, a heterocyclyl group, an acyl group derived from a carboxylic or a substituted carbamic acid, or a group $CR^{10}R^{11}R^{12}$;
$R^7$ represents a hydrogen atom or an optionally substituted alkyl or aryl group;
Z represents a hydroxy, alkoxy, acyloxy, amino, alkylamino or dialkylamino group;
$R^3$ represents a hydrogen atom or an optionally substituted alkyl group;
each of $R^4$ and $R^5$ independently represents a hydrogen atom or an optionally substituted alkyl group;
each of $R^8$ and $R^9$ independently represents a hydrogen atom, an alkyl group or an aryl group;
each of $R^{10}$ and $R^{11}$ independently represents a hydrogen atom or an alkyl group;
$R^{12}$ represents an alkoxyalkoxy group a heterocyclyl group, an alkoxycarbonyl group, an optionally substituted aryl group, an alkylthio group or a substituted carboxamido group; and
Ar represents an optionally substituted fully unsaturated ring having 5 or 6 atoms in the ring of which one is a nitrogen atom and the remainder are carbon atoms, or the N-oxide or an acid addition salt thereof, or Ar represents an optionally substituted phenyl group;
with the proviso that if both X and Y represent groups $CR^6R^7$, at least one substituent $R^6$ is a group —OA; exhibit useful herbicidal activity.

10 Claims, No Drawings

HERBICIDAL TETRAHYDROFURAN DERIVATIVES

CROSS-REFERENCE TO RELATED APPLICATIONS

This application is a continuation-in-part of U.S. Ser. No. 225,950, filed Jan. 19, 1981, now abandoned.

BACKGROUND OF THE INVENTION

1. Field of the Invention

The present invention relates to certain novel tetrahydrofuran derivatives, herbicidal compositions containing them and a method of controlling undesirable plant growth using them.

2. Description of the Prior Art

U.S. Pat. No. 4,116,669, German Offenlegungschift 2,749,974 and European Pat. No. 13,581 disclose that certain tetrahydrofuran derivatives are useful as herbicides. It has now been found that certain other novel tetrahydrofuran derivatives also have useful herbicidal properties.

DESCRIPTION OF THE INVENTION

The present invention provides a tetrahydrofuran derivative of the general formula

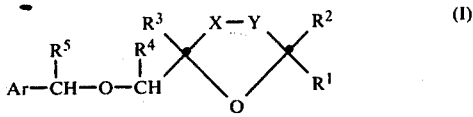

wherein
each of $R^1$ and $R^2$ independently represents a hydrogen atom or an optionally substituted alkyl, cycloalkyl or aryl group, or $R^1$ and $R^2$ together represent an optionally substituted alkylene group;
each of X and Y independently represents one of the groups $CR^6R^7$, $C=O$, $C=N-Z$, $CH-NH_2$,

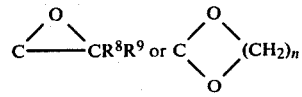

in which
n is 2 or 3;
$R^6$ represents a hydrogen atom, an optionally substituted alkyl or aryl group, or a group of formula $-OA$ in which A represents a hydrogen atom, an acyl group derived from a carboxylic or a substituted carbamic acid, a heterocyclyl group, or a group $CR^{10}R^{12}$;
$R^7$ represents a hydrogen atom or an optionally substituted alkyl or aryl group;
Z represents a hydroxy, alkoxy, acyloxy, amino, alkylamino or dialkylamino group;
$R^3$ represents a hydrogen atom or an optionally substituted alkyl group;
each of $R^4$ and $R^5$ independently represents a hydrogen atom or an optionally substituted alkyl group;
each of $R^8$ and $R^9$ independently represents a hydrogen atom, an alkyl group or an aryl group;
each of $R^{10}$ and $R^{11}$ independently represents a hydrogen atom or an alkyl group;
$R^{12}$ represents an alkoxyalkoxy group, a heterocyclyl group, an alkoxycarbonyl group, an optionally substituted aryl group, an alkylthio group or a substituted carboxamido group; and
Ar represents an optionally substituted fully unsaturated ring having 5 or 6 atoms in the ring of which one is a nitrogen atom and the remainder are carbon atoms, or the N-oxide or an acid addition salt thereof, or Ar represents an optionally substituted phenyl group;
with the proviso that if both X and Y represent groups $CR^6R^7$, at least one substituent $R^6$ is a group $-OA$.

The optional substituents in an optionally-substituted group referred to in the definition of the general formula I may for example be one or more of the same or different substituents selected from halogen atoms, especially chlorine and fluorine atoms, and alkyl, alkoxy, alkylthio, aryl and aryloxy groups. Unless otherwise stated, any alkyl moiety in a compound of formula I preferably has up to 6 carbon atoms. The cycloalkyl groups have from 3 to 7 carbon atoms and the aryl groups containing from 6 to 10 carbon atoms and 1 to 2 carbon rings.

Preferably each of $R^1$ and $R^2$ independently represents a hydrogen atom, an alkyl group having up to 6 carbon atoms, or a substituted or unsubstituted phenyl group, or $R^1$ and $R^2$ together represent an alkylene group having up to 6 carbon atoms. More preferably, each of $R^1$ and $R^2$ independently represents a hydrogen atom, a methyl group or an ethyl group, or $R^1$ and $R^2$ together represent a pentamethylene group.

Preferably $R^3$ represents a hydrogen atom or an alkyl group having up to 6 carbon atoms which may be unsubstituted or substituted. More preferably $R^3$ represents a methyl, ethyl, halomethyl or methoxymethyl group.

Preferably each of $R^4$ and $R^5$ represents a hydrogen atom.

Preferably Ar represents a ring as defined above which may be unsubstituted or substituted by one or more of the same or different substituents selected from halogen atoms, expecially chlorine or fluorine atoms, and alkyl groups having up to 6 carbon atoms, especially methyl or ethyl groups. Preferably Ar represents an optionally substituted phenyl group, especially an unsubstituted phenyl group or a 2-methyl-, 2-fluoro-, 2-chloro- or 2,6-dichloro-phenyl group.

By optionally-substituted fully unsaturated groups there should be understood optionally-substituted pyridyl, pyrrolyl and azacyclopentadiene groups. Thus the group Ar may for example represent one of the groups:

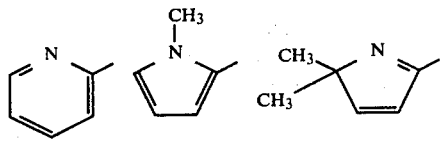

If Ar represents a heterocyclic group, this group is preferably bonded to the rest of the molecule through a carbon atom, and the nitrogen atom in the ring is preferably adjacent to this carbon atom. For example Ar may represent a 2-pyridyl group which is unsubstituted or substituted in the 3- or the 6-position by a chlorine or fluorine atom or by a methyl or ethyl group. As stated above, the invention includes N-oxides and salts of compounds of the general formula I in which Ar is a heterocyclic group. A salt may be any non-phytotoxic anion, for example, an acid addition salt or a quaternary ammonium salt, for example a compound of the general formula

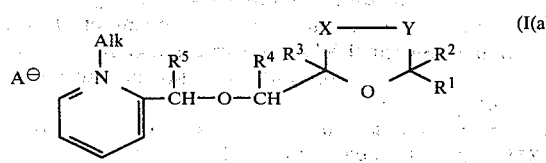

in which Alk represents an alkyl group having up to 6 carbon atoms, especially a methyl or an ethyl group, and $A^-$ represents one equivalent of an anion, especially a halogen ion, for example an iodide or chloride ion, or one equivalent of a sulphate ion. From the halides, other non-phytotoxic salts can be prepared by known methods, such as the nitrate, sulphonate, trifluoromethansulfonate, chlorate, acetate, borate, tartrate, succinate, phosphate, etc.

Preferably $R^6$ represents a hydrogen atom, a methyl group, or a group of formula —OA in which A represents a hydrogen atom, a heterocyclyl group, an alkylcarbonyl group, an aminocarbonyl group substituted by 1 or 2 alkyl and/or phenyl groups, or an alkoxyalkoxymethyl group having up to 7 carbon atoms. More preferably, $R^6$ represents a hydrogen atom or a group of formula —OA in which A represents a hydrogen atom, an acetyl group, a phenylaminocarbonyl group or a methoxyethoxymethyl group. If A represents a heterocyclyl group, this is preferably a 5 or 6 membered ring containing one or more oxygen, sulphur and/or nitrogen atoms, preferably one or two nitrogen atoms. For example, A may represent a pyridyl, imidazolyl or pyrimidyl group.

Preferably $R^7$ represents a methyl group or, especially, a hydrogen atom.

Preferably Z represents a hydroxy or amino group or an alkylamino, dialkylamino, alkoxy or alkylcarbonyloxy group having up to 4 carbon atoms in the or each alkyl group.

Preferably each of $R^8$ and $R^9$ represents a hydrogen atom.

Preferably, one of X and Y represents a group selected from CHOA, C=O, C=NOH, CH—NH$_2$,

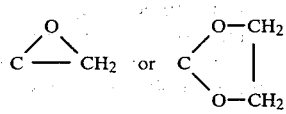

wherein A represents a hydrogen atom; an alkylcarbonyl group of up to 7 carbon atoms; a phenylaminocarbonyl group optionally substituted in the phenyl ring by one or more substituents independently selected from halogen atoms and alkyl groups of up to 6 carbon atoms; a 2-pyrimidinyl group; an alkoxyalkoxymethyl group of up to 7 carbon atoms; an alkoxycarbonylmethyl group of up to 7 carbon atoms; a benzyl group optionally substituted by one or more substituents independently selected from halogen atoms, alkyl groups of up to 6 carbon atoms and a phenoxy group; an alkylthiomethyl group of up to 7 carbon atoms; or an anilinocarboxyamidomethyl group optionally substituted in the phenyl ring by one or more substituents independently selected from halogen atoms and alkyl groups of up to 6 carbon atoms. Also it is preferred for one of X and Y, advantageously X, to represent a CH$_2$ group or preferably one of X and Y represents a CH$_2$ group and the other represents a C=O group or a group CR$^6$R$^7$ in which $R^6$ is a group —OA.

The compounds of the general formula I exist in the form of optical isomers, and may also exist as geometric isomers, depending on the substituents present in the molecule. It should be understood that the present invention includes all such isomers and mixtures thereof.

Compounds of formula I may be prepared by a process which comprises reacting an alkali metal or alkaline earth metal salt of a compound of general formula III

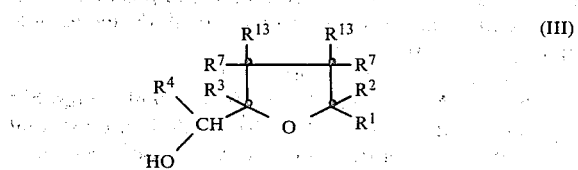

wherein $R^1$, $R^2$, $R^3$, $R^4$ and $R^7$ are as defined above, one $R^{13}$ represents a hydrogen atom, an optionally substituted alkyl or aryl group or a group $OR^{14}$, and the other $R^{13}$ represents a group $OR^{14}$, $R^{14}$ being a protecting group which can be removed to generate a free hydroxy group with a compound of general formula IV

wherein Ar and $R^5$ are as defined above and Hal is a halogen atom, and, optionally where $R^{14}$ represents a group A as defined above, converting a group CR$^7$OR$^{14}$ into a group X or Y as defined above to produce the compound of formula I.

The compound of formula III may be prepared by epoxidising a compound of general formula II

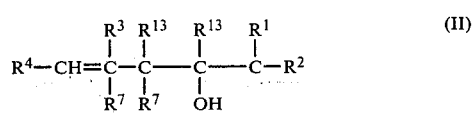

wherein $R^1$, $R^2$, $R^3$, $R^4$, $R^7$ and $R^{13}$ are as defined above with an electrophilic epoxidising agent and cyclising to produce compound of formula II, which is then converted into an alkali metal salt for reaction with the compound of formula IV.

Suitable electrophilic epoxidising agents include hydrogen peroxide, alkali metal peroxides or hypohalites, metal perborates, peroxyacetyl nitrate and silver oxide. Especially suitable electrophilic epoxidising agents are peroxyacids, for example aliphatic peroxyacids such as peroxyacetic acid or peroxyformic acid, or, preferably, aromatic peroxyacids such as unsubstituted or substituted peroxybenzoic acid. Especially suitable are halogen-substituted peroxybenzoic acids, for example acids in which the phenyl ring is substituted by one or two chlorine and/or bromine atoms. Meta-chloroperoxybenzoic acid is especially suitable.

The reaction is suitably carried out in the presence of an inert solvent, for example a hydrocarbon, chlorinated hydrocarbon, ether or ester, such as benzene, toluene, methylene chloride, carbon tetrachloride, diethyl ether or ethyl acetate. Mixtures of solvents may be suitable.

The reaction is preferably carried out at a temperature in the range of from −10° C. to 80° C., especially 0° to 20° C. It may in some cases be convenient to carry out the reaction at the reflux temperature of the solvent used.

The molar ratio of the compound of the general formula II and the electrophilic epoxidising agent is not of critical importance. Preferably the compound of the general formula II and the electrophilic epoxidising agent are mixed in approximately equimolar quantities, or a slight excess of the epoxidising agent is used. Preferably the molar ratio of the compound of the general formula I to the electrophilic epoxidising agent is in the range of from 1:1 to 1:2 especially 1:1 to 1:1.5. Useful yields can however be obtained using a molar ratio of up to 1:10 or higher.

If desired, the resulting compound of the general formula III may be extracted from the reaction mixture by any suitable work-up procedure. However, it may be advantageous to carry out a further chemical reaction using the compound of the general formula III either after its isolation or directly in situ in the reaction mixture.

The oxolane alcohol of formula III may be converted into a salt thereof by reaction with a base. Alkali metal hydroxides, alkoxides or hydrides are suitable bases. The alcohol may be converted into its salt prior to admixing it with the compound of formula IV, or the salt may be formed in situ by admixing the compounds of the formulae III and IV in the presence of a base. Any suitable solvent may be used for the reaction, for example an aromatic hydrocarbon, for example benzene or toluene. The reaction may for example be carried out at a temperature in the range of from 50° to 150° C. Conveniently, the reaction is carried out at the reflux temperature of the solvent used.

Compounds of the general formula II may be prepared by methods analogous to known methods.

Compounds of the general formula I(b) as described above, may be regarded as examples of compounds in which a hydroxy group is protected by a $CR^{10}R^{11}R^{12}$ group, which group can easily be removed to generate the free alcohol. The invention further provides a process for the preparation of a compound of the general formula I with the exception of those compounds in which each of X and Y represents a $CR^6R^7$ group, and one of $R^6$ represents a hydrogen atom, an optionally substituted alkyl or aryl group, or a group $OCR^{10}R_{11}R^{12}$, and the other represents a group $OCR^{10}R^{11}R^{12}$, which comprises preparing a compound of the general formula

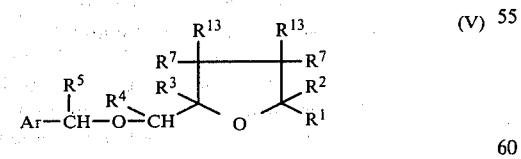

(V)

in which $R^1$, $R^2$, $R^3$, $R^4$, $R^5$ $R^7$ and Ar have the meanings given for the general formula I, and one $R^{13}$ represents a hydrogen atom, an optionally substituted alkyl or aryl group or a group $OR^{14}$, and the other $R^{13}$ represents a group $OR^{14}$, $R^{14}$ being a protecting group which can be removed to generate a free hydroxy group, and then removing said group $R^{14}$ to produce a compound of the general formula I in which at least one of X and Y is a $C.OH.R^7$ group; and optionally converting the resulting compound into any other required compound of the general formula I.

The protecting group $R^{14}$ must be a group which can be replaced by a hydrogen atom to generate a hydroxy group without causing cleavage of the tetrahydrofuran ring. One of the most suitable methods of protecting a hydroxy group involves ketal, thioketal, acetal or thioacetal formation, since such groups can be cleaved to regenerate the hydroxy group by treatment with an acid under mild conditions. Thus suitable groups $R^{14}$ include, as well as $CR^{10}R^{11}R^{12}$ groups, alkoxymethyl, alkylthiomethyl, aryloxymethyl and arylthiomethyl groups. Preferably $R^{14}$ is an alkoxyalkoxymethyl or alkoxymethyl group having up to 7 carbon atoms.

The starting materials containing the group $R^{14}$ may be prepared in the same manner as described above for the case in which $R^{14}$ is a $CR^{10}R^{11}R^{12}$ group. In order to prepare some compounds of the general formula I in which X and Y have different meanings, it may be desirable to prepare starting compounds containing two different $R^{14}$ groups, so that one group $R^{14}$ may be selectively removed, the resulting $C.OH.R^7$ group may be further reacted, and the second $R^{14}$ group may then be removed.

A compound of the general formula I in which one or both of X and Y is a group $C.OH.R^7$, may be converted into other compounds of the general formula I by methods analogous to methods known in the art. Such methods include the following.

1. The —OH group may be esterified using a carboxylic acid or an acyl halide or the anhydride thereof. The conditions usual for the preparation of esters may be used. For example, the reactants may be mixed in the presence of an inert solvent and in the presence of an acidic or basic catalyst. Mild conditions which do not result in cleavage of the tetrahydrofuran ring should of course be used.
2. The —OH group may be converted into an ester group derived from a substituted carbamic acid by reaction with an isocyanate in the presence of a base. Organic bases such as tertiary amines, for example triethylamine, are suitable.
3. The hydroxy group may be oxidised to form the corresponding ketone. Any suitable oxidising agent, for example manganese dioxide, potassium permanganate or a chromium salt, may be used.
4. A compound of the general formula I in which one or both of X and Y is C=O, may be converted into the corresponding compound in which one or both of X and Y is C=N—Z, by treatment with hydroxylamine to produce a compound in which Z is OH, or with hydrazine in which one or both hydrogen atoms on one nitrogen atom may be replaced by an alkyl group, to form a compound in which Z is amino, alkylamino or dialkylamino. Compounds in which Z is alkoxy or acyloxy may be prepared by reacting a compound in which Z is hydroxy with an alkyl or acyl halide in the presence of a base.
5. A compound of the general formula I in which one or both of X and Y is C=O, may be converted into the corresponding compound in which one or both of X and Y is

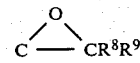

by reaction with a methylene transfer agent, for example diazomethane, dimethyl oxosulphonium methylide or dimethylsulphonium methylide, in an inert solvent, for example dimethylsulphoxide, or by reaction with a Wittig reagent.

6. A compound of the general formula I in which one or both of X and Y is C=O, may be converted into the corresponding compound in with one or both of X and Y is

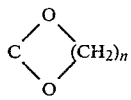

by reaction with a compound of formula HO—$(CH_2)_n$—OH, for example ethylene glycol in the pressure of an acid catalyst. The reaction is suitably carried out in an inert solvent, such as benzene. If n is 2, the ketone may be reacted with ethylene oxide in the presence of a catalyst, suitably a Lewis acid, to produce the desired compound.

7. A compound of general formula I wherein one or both of X and Y is C=NOH may be converted to the corresponding compound wherein one or both of X and Y is CH—$NH_2$ by treatment with an appropriate reducing agent, e.g. lithium aluminium hydride.

8. The hydroxy group may be converted into a group $CR^{10}R^{11}R^{12}$ by treatment firstly with a strong base such as sodium hydride and secondly with an appropriate halide $HalCR^{10}R^4R^{12}$ where Hal is a chlorine, bromine or iodine atom. Where the group $R^{12}$ is an alkoxycarbonyl group or a substituted carboxamido group, the hydroxy group may be converted by treatment firstly with the strong base and secondly with a haloacetic acid derivative Hal $CR^{10}R^{11}COOH$, followed by appropriate conversion of the —COOH function to the alkoxycarbonyl or substituted carboxamide group in known manner.

The compounds of general formula I exhibit herbicidal activity. Therefore the invention further provides a herbicidal composition which comprises a compound of the formula I together with a suitable carrier. The invention also provides a method of combating undesired plant growth at a locus, which comprises applying to the locus a compound or a composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonates; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants of stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676-0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The composition of the invention may also contain other ingredients, for example, other compounds possessing herbicidal, insecticidal or fungicidal properties.

The following Examples illustrate the invention. NMR values are δ values relative to tetramethylisilane in CDCl$_3$.

EXAMPLE 1

2,2-Dimethyl-3-methoxyethoxyethoxymethoxy-5-benzyloxymethyl-5-ethyloxolane (a) 5.9 g sodium were dissolved in 300 ml abolute ethanol and ethyl acetoacetate (31.72 g) was added. The mixture was stirred for 15 minutes, 2-bromomethylbut-1-ene (40 g) was added over 30 minutes, and the mixture was then refluxed for 2 hours. The mixture was then poured onto brine, extracted several times with diethyl ether, washed with brine, dried and evaporated down. Distillation of the residue under vacuum gave 29 g, corresponding to a 60% yield, of 2-ethyl-4-methylcarbonyl-4-ethoxycarbonylbut-1-ene, boiling point 120°-127° C. at a pressure of 10 mm Hg.

(b) The product from (a) (25 g) was added to 6.2 g of a 50% suspension of sodium hydride in oil dissolved in benzene (250 ml) and stirred for two hours. Dibenzoyl peroxide, (C$_6$H$_5$CO$_2$)$_2$, (20.4 g) in benzene (200 ml) was added over 30 minutes. The mixture was stirred for a further 2 hours, and then poured onto water and extracted several times with diethyl ether, dried, and distilled under vacuum to give 24 corresponding to a yield in step (b) of 89.5%, of 2-ethyl-4-methylcarbonyl-4-ethoxycarbonyl-4-benzoyloxybut-1-ene, boiling point 160° C. at pressure of 1 mm Hg.

(c) Sodium (250 mg) was dissolved in dry ethanol (250 ml) and the product from (b) above (22.65 g) was added. The mixture was stirred overnight and then refluxed for 2 hours. Ammonium chloride (0.5 g) and water (0.25 ml) were added and stirring was continued for ½ hour. The mixture was then filtered and the solvent was evaporated. The residue was dissolved in diethyl ether, the mixture was filtered and the ether evaporated off to leave 2-ethyl-4-hydroxy-4-ethoxycarbonylbut-ene which was identified by NMR. This residue was dissolved in methylene chloride (200 ml) containing methoxyethoxymethyl chloride (12.5 ml) and ethyl disopropylamine (22.5 ml) and the mixture was stirred overnight. A further 5 ml methoxyethoxymethyl chloride and 10 ml ethyl diisopropylamine were added.

The mixture was refluxed for 3 hours and then poured onto water, washed with 10% hydrochloric acid and then brine, dried over potassium carbonate and evaporated down. The residue was eluted down a silica gel comumn using methylene chloride. The solvent was then evaporated and the product was distilled. 14.5 g of 2-ethyl-4-methoxyethoxymethoxy-4-ethoxycarbonylbut-1-ene, boiling point 158°-162° C. at a pressure of 12 mm Hg, were obtained.

(d) Magnesium (3.3 g) was dissolved in a solution of methyl iodide (19.1 g) in diethyl ether, and an ethereal solution of 14 g of the ester prepared in (c) above was added to the refluxing solution over 20 minutes. The mixture was then stirred for a further 2 hours. Saturated ammonium chloride solution was then added, the mixture was extracted with diethyl ether, washed with brine, dried over magnesium sulphate and evaporated down. The residue was distilled to obtain 9.5 g of 2-ethyl-4-methoxyethoxymethoxy-5-hydroxy-5-methylehex-1-ene, boiling at 115°-120° C. at a pressure of 2 mm Hg. Its NMR spectrum was as follows: 0.9(3H,triplet); 1.2(6H,singlet); 1.8-2.3(4H,complex) 3.2(1H, broad); 3.3(3H,singlet); 3.5(5H,complex); 4.7(4H,complex).

(e) The olefinic alcohol prepared in (d) (9.5 g) was dissolved in methylene chloride and added to m-chloroperoxybenzoic acid (8.65 g of 85% pure material) in methylene chloride at 0° C. over 30 minutes. The mixture was stirred for 20 hours, and then washed successively with aqueous solutions of sodium sulphite, sodium bicarbonate and sodium chloride, and dried. The solvent was evaporated to leave a crude product which was identified as a mixture of isomers of 2,2-dimethyl-3-methoxyethoxymethoxy-5-hydroxymethyl-5-ethoxyloxolane, using NMR, as follows: 0.9(3H,triplet); 1.2(6H, doublet); 1.4-2.5(5H,complex); 3.3(3H, singlet); 3.4-4.1(7H,complex); 4.7(2H,singlet)

(f) The whole of the crude product obtained in (e) was dissolved in toluene (80 ml) and was added with stirring to a solution of sodium hydride (2.15 g of a 50% suspension in oil) in dry toluene (150 ml) over 15 minutes.

The mixture was refluxed for 40 minutes, and benzyl bromide (8.25 g) in toluene (50 ml) was then added dropwise. Refluxing and stirring was continued for 18 hours. The mixture was then poured onto brine, extracted with diethyl ether and dried over magnesium sulphate. The solvent was removed to give 17.5 g of crude material, which was purified on a silica gel column using acetone/petrol as eluant, to give 8.2 g of the pure desired product. NMR showed that a mixture of geometric isomers was present.

NMR: 0.9(3H,triplet); 1.2(6H,doublet); 1.4-2.4(4H,complex); 3.3(3H,singlet); 3.5(6H,complex); 4.1(1H,broad triplet); 4.5(2H,singlet); 4.7(2H,singlet); 7.2(5H,singlet).

| Elemental Analysis | C | H |
| --- | --- | --- |
| Calculated for C$_{20}$H$_{32}$O$_5$ | 68.15 | 9.5 |
| Found | 67.5 | 9.7 |

EXAMPLE 2

2,2-Dimethyl-3-methoxymethoxymethoxy-5-benzyloxymethyl-5-methyloxolane

The title compound was prepared by a method analogous to that described in Example 1 using 2-bromomethylpropene as starting material. NMR showed the product to be a mixture of geometric isomers.

NMR: 1.2(9H,singlet); 1.5–2.5(2H,complex); 2.3(3H,singlet); 3.4(6H, complex); 3.9(1H,broad triplet); 4.4(2H,singlet); 4.6(2H,broad singlet); 7.2(5H,singlet).

| Elemental Analysis | C | H |
|---|---|---|
| Calculated for $C_{19}H_{30}O_5$ | 67.4 | 8.94 |
| Found | 67.4 | 9.3 |

EXAMPLE 3

2,2-Dimethyl-3-hydroxy-5-benzyloxymethyl-5-ethyloxolane

The compound of Example 1 (33.5 g) was added to methanol (500 ml) containing 5 ml concentrated hydrochloric acid, and the resulting mixture was refluxed for 2½ hours. It was then cooled, the solvent was evaporated off and the residue was dissolved in diethyl ether. The solution was washed with neutral brine, dried over magnesium sulphate and evaporated to give 25.1 g of the desired product. This corresponds to a 100% yield. NMR showed the product to be a mixture of geometric isomers.

NMR: 0.9(3H,triplet); 1.2(6H, multiplet); 1.4–2.4(4H,complex); 3.2 and 3.4(2H,two singlets); 3.7(1H,broad); 4.1(1H,multiplet); 4.4 and 4.5(2H,two singlets); 7.3(5H,singlet).

| Elemental Analysis | C | H |
|---|---|---|
| Calculated for $C_{16}H_{24}O_3$ | 72.7 | 9.15 |
| Found | 72.6 | 9.8 |

EXAMPLE 4

2,2-Dimethyl-3-acetoxy-5-benzyloxymethyl-5-ethyloxolane

The alcohol of Example 3 (800 mg) was added to pyridine (20 ml) and acetic anhydride (5 ml) and the mixture was stirred at room temperature over two days. The mixture was then evaporated down under vacuum and the residue was dissolved in diethyl ether. The solution was decolourised over charcoal, and the ether was removed to give 860 mg of the desired product. NMR showed that the product was a mixture of geometric isomers.

NMR: 0.9(3H,broad triplet); 1.2(6H,doublet); 1.9 and 2.0(3H, two singlets); 1.4–2.6(4H,complex); 3.3 and 3.4(2H, two singlets); 4.5(2H,singlet); 5.0(1H,multiplet); 7.3(5H,singlet).

EXAMPLE 5

2,2-Dimethyl-3-(N-phenylaminocarbonyloxy)-5-benzyloxymethyl-5-ethyloxolane

The alcohol of Example 3 (1 g) was dissolved in benzene (15 ml) and phenylisocyanate (600 mg) and a few drops of triethylamine were added. The mixture was refluxed for 20 hours. The solvent was then evaporated and the residue was taken up in ethyl acetate, washed with dilute hydrochloric acid and then with brine, dried over magnesium sulphate and evaporated down. The residue was purified on a silica column using 5% acetone in petrol as eluant. 1.4 g, corresponding to a 100% yield, of the desired product, as a viscous oil, were obtained. NMR showed the presence of both geometric isomers.

NMR: 0.9(3H,broad triplet); 1.3(6H, broad doublet); 1.5–2.6(4H,complex); 3.3 and 3.4(2H,two singlets); 4.5(2H,singlet); 5.1(1H,multiplet); 6.3–7.2(3H,complex); 7.3(8H,singlet).

EXAMPLE 6

2,2-Dimethyl-5-benzyloxymethyl-5-ethyloxolane-3-one

The alcohol of Example 3 (16 g), methylene chloride (300 ml) and pyridinium chlorochromate (14.5 g) were stirred over two days at room temperature. The solution was filtered through a column of Fluorosil using methylene chloride as eluant. Evaporation of the solvent gave 15.8 g, corresponding a 100% yield, of the desired product, which solidified on cooling.

NMR: 0.9(3H,triplet); 1.2(3H,singlet); 1.3(3H,singlet); 1.6(2H,quadruplet); 2.5(2H,quadruplet); 3.4(2H,singlet); 4.5(2H,singlet); 7.2(5H,singlet).

EXAMPLE 7

2,2-Dimethyl-3-hydroxyimino-5-benzyloxymethyl-5-ethyloxolane

The ketone of Example 6 (1 g), ethanol (20 ml) hydroxylamine hydrochloride (280 mg) and potassium carbonate (330 mg) were refluxed together for 2 hours. Thin layer chromatography, using 15% acetone in petrol as eluant, showed partial conversion. Additional quantities of hydroxylamine hydrochloride (280 mg) and potassium carbonate (330 mg) were added three times, with refluxing for 2 hours after each addition. Water was then added, and the mixture was extracted with diethyl ether. The ether extract was dried over magnesium sulphate and evaporated and the residue was purified on a silica gel column using 5% acetone in petrol as eluant to give 1 g (94%) of the desired product.

NMR: 0.7(3H,triplet); 1.35(6H,singlet); 1.55(2H,quadruplet); 2.75 (2H,quadruplet); 3.3(2H,singlet); 4.5(2H,singlet); 7.25(5H,singlet); 9.1(1H,broad).

| Elemental Analysis | C | H | N |
|---|---|---|---|
| Calculated for $C_{16}H_{23}O_3N$ | 69.3 | 8.36 | 5.05 |
| Found | 68.9 | 8.8 | 4.7 |

EXAMPLE 8

2,2-Dimethyl-5-benzyloxymethyl-5-ethyl oxolane-3-spirooxirane 230 mg of a 50% suspension of sodium hydride in oil was washed once with dry petrol, and 20 ml of dry dimethylsulphoxide was added under a nitrogen atmosphere. 1 g of trimethylsulfoxyiodide was added over 15 minutes. Hydrogen evolved and the mixture was stirred for a further 30 minutes. 1 g of the ketone of Example 6 was added over 5 minutes, the mixture was heated at 55°–60° C. for 20 minutes and was allowed to stand for 2 hours at ambient temperature. The mixture was then poured onto excess water and extracted twice with diethyl ether. The combined ether extracts were washed with water, dried over magnesium sulphate and evaporated to yield a residue which was purified on a silica gel column using methylene chloride as eluant to give 400 mg of the desired product.

NMR: 1.0(9H,multiplet); 1.5–3.0(3H,complex); 3.4(2H,broad singlet); 4.5(2H,singlet); 7.2(5H,singlet).

| Elemental Analysis | C | H |
|---|---|---|
| Calculated for $C_{17}H_{24}O_3$ | 73.9 | 8.75 |
| Found | 72.0 | 9.0 |

EXAMPLE 9

2,2-Dimethyl-3-(2-pyrimidinyloxy)-5-benzyloxymethyl-5-ethyloxolane 1 g of the alcohol of Example 3 was added to 220 mg of a 50% suspension of sodium hydride in oil dissolved in toluene (15 ml) and the mixture was stirred under reflux for 1 hour. 2-pyrimidinyl chloride (625 mg) in 10 ml toluene was added over 30 minutes. The mixture was stirred at reflux temperature for 16 hours. The mixture was then poured into brine and extracted with diethyl ether. The ether extract was dried over magnesium sulphate and evaporated to yield a residue which was purified on a silica gel column using 8% acetone in petrol as eluant to give 1.25 g (97%) of the desired product.

NMR: 0.9(3H,triplet); 1.35(6H,singlet); 1.5–2.75(4H,complex); 3.4–3.5(2H,singlet); 4.5–4.6(2H,singlet); 5.35(1H,quadruplet); 6.9(1H,triplet); 7.2–7.5(5H,multiplet); 8.5(2H,doublet).

| Elemental Analysis | C | H | N |
|---|---|---|---|
| Calculated for $C_{20}H_{26}N_2O_3$ | 70.2 | 7.6 | 8.2 |
| Found | 69.4 | 7.8 | 8.0 |

EXAMPLE 10

2,2-Dimethyl-3-(2-pyridylmethoxy)-5-benzyloxymethyl-5-ethyloxolane

This compound was prepared by a method similar to that of Example 9.

NMR: 0.8(3H,triplet); 1.2(6H,singlet); 1.4–2.5(6H,complex); 3.3(2H,doublet); 3.8(1H,multiplet); 4.5(2H,singlet); 4.6(2H,singlet); 6.7(8H,complex) and 8.5(1H,broad doublet).

| Elemental Analysis | C | H | N |
|---|---|---|---|
| Calculated for $C_{22}H_{29}NO_3$ | 74.3 | 8.22 | 3.94 |
| Found | 71.9 | 8.4 | 3.80 |

EXAMPLE 11

2,2-Dimethyl-3-(methoxycarbonylmethoxy)-5-benzyloxymethyl-5-ethyloxolane 1 g of the alcohol of Example 3 dissolved in dry toluene (5 ml) was added to 460 mg of a 50% suspension of sodium hydride in oil in dry toluene (10 ml) and the mixture was stirred at reflux temperature under nitrogen for 1 hour. 355 mg of chloroacetic acid in toluene (10 ml) was added carefully over 30 minutes and the mixture was stirred at reflux temperature for 17 hours. The resulting solution was cooled and poured into water. The mixture was washed with diethyl ether and the ethereal phase was extracted with sodium bicarbonate solution. The aqueous extracts were combined and were acidified with concentrated hydrochloric acid. The oil which precipitated out was extracted (twice) with diethyl ether. The ether extracts were washed with brine, dried over magnesium sulphate and evaporated to yield 1 g of the intermediate, 2,2-dimethyl-3-(hydroxycarboxymethoxy)-5-benzyloxy-5-ethyloxolane, as an oil.

This intermediate was dissolved in 30 ml of dry methanol and 0.5 ml of concentrated sulphuric acid was added. The mixture was left for 17 hours and was then poured into excess water. The mixture was extracted three times with diethyl ether. The combined ether extracts were washed with aqueous sodium bicarbonate solution, dried over magnesium sulphate and evaporated giving 1 g (78%) of the desired product as an oil.

NMR: 0.8(3H,triplet); 1.2(6H,multiplet); 1.25–2.5(4H,complex); 3.25 (2H,doublet); 3.6(3H,singlet); 4.0(2H,multiplet); 3.8(1H,multiplet); 4.5(2H,singlet); 7.2(5H,singlet).

| Elemental Analysis | C | H |
|---|---|---|
| Calculated for $C_{19}H_{28}O_5$ | 67.83 | 8.4 |
| Found | 67.8 | 8.6 |

EXAMPLE 12

2,2-Dimethyl-3-(2-dioxanyl)-5-benzyloxymethyl-5-ethyloxolane 1 g of the ketone of Example 6, 250 mg of ethylene glycol and a few milligrams of para-toluenesulphonic acid in 20 ml benzene were heated at reflux temperature in a Dean/Stark apparatus for 16 hours. The resulting mixture was washed with aqueous sodium bicarbonate solution, dried over magnesium sulphate and evaporated to give 1.16 g crude material which was purified on a silica gel column using 3% acetone in petrol as eluant to give 1.0 g (86%) of the desired product.

NMR: 0.8(3H,triplet); 1.2(6H,singlet); 1.6(2H, multiplet); 2.0(2H,quadruplet); 3.3(2H,singlet); 3.8(4H,singlet); 4.5(2H,singlet); 7.2(5H,singlet).

EXAMPLE 13

2,2-Dimethyl-3-(3-phenoxybenzyloxy)-5-benzyloxymethyl-5-ethyloxolane

This compound was prepared by a method similar to that of Example 9.

NMR: 0.8(3H,triplet); 1.2(6H,broad singlet); 1.4–2.4(4H,complex); 3.3(2H,doublet); 3.8(1H,multiplet); 4.4(4H,multiplet); 7.1(14H,multiplet).

| Elemental Analysis | C | H |
|---|---|---|
| Calculated for $C_{29}H_{32}O_4$ | 78.35 | 7.26 |
| Found | 76.6 | 7.7 |

EXAMPLE 14

2,2-Dimethyl-3-amino-5-benzyloxymethyl-5-ethyl oxolane 1.9 g of the hydroxyimino compound of Example 7 in 5 ml of diethyl ether was added to 260 mg of lithium aluminium hydride in 25 ml of diethyl ether, and the resulting mixture was stirred at reflux temperature for 2 hours. A further 100 mg of lithium aluminium hydride was added and stirring at reflux temperature was continued for 1 hour. 0.36 ml of water was then added to the reaction mixture, followed by 0.36 ml of 15% solution of sodium hydroxide and a further 1.08 ml of water. The mixture was then filtered and evaporated to dryness. Thin layer chromatography indicated that the residue contained some unconverted starting material. The desired amine product was obtained from the residue by extracting the residue twice into dilute hydrochloric acid, washing the extracts with diethyl ether, rendering the aqueous phase alkaline by addition of dilute sodium hydroxide solution, saturating the aqueous phase with sodium chloride and extracting the amine by washing three times with diethyl ether. The combined ether extracts were dried over magnesium sulphate and evaporated to give 1.0 g (50%) of the desired product. The product was a mixture of two isomers which were shown to be separable using thin-layer chromatography on silica gel using 20% acetone in petrol as eluant.

NMR: 0.8(3H,triplet); 1.0–1.4(6H,complex); 1.4–2.4(6H,complex); 3.25(3H,multiplet); 4.5(2H,multiplet); 7.2(5H,singlet).

| Elemental Analysis | N |
|---|---|
| Calculated for $C_{16}H_{25}NO_2$ | 5.32 |
| Found | 5.0 |

EXAMPLE 15

2,2-Dimethyl-3-methoxyethoxymethoxy-5-(2-fluorobenzyloxymethyl)-5-ethyl oxolane

This compound was prepared by a method similar to that described in Example 1, substituting 2-fluorobenzylchloride for the benzyl bromide in step (f). (Yield 71%).

NMR: 0.85(3H,triplet); 1.15–1.25(6H,singlet); 1.35–2.5(4H,complex); 3.2–4.2(10H,overlapping signals including a singlet and a quadruplet); 4.6(2H,singlet); 4.7(2H,singlet); 6.8–7.6(4H,complex).

| Elemental Analysis | C | H |
|---|---|---|
| Calculated for $C_{20}H_{31}O_5F$ | 64.9 | 8.4 |
| Found | 65.4 | 8.8 |

EXAMPLE 16

2,2-Dimethyl-3-hydroxy-5-(2-fluorobenzyloxymethyl)-5-ethyloxolane

This compound was prepared from the compound of Example 15 by a method similar to that described in Example 3. (Yield 83%)

NMR: 0.85(3H,double triplet); 1.15–1.3(6H,singlet); 1.4–2.5(4H,complex); 3.35–3.4(2H,singlet); 3.6–4.4(1H,complex); 2.6–2.65(2H,singlet); 6.8–7.6(4H,complex).

| Elemental Analysis | C | H |
|---|---|---|
| Calculated for $C_{16}H_{23}O_3F$ | 68.1 | 8.15 |
| Found | 68.6 | 9 |

EXAMPLE 17

2,2-Dimethyl-3-methoxyethoxymethyl-5-(2-pyridylmethoxymethyl)-5-ethyl oxolane

This compound was prepared by a method similar to that described in Example 1, the benzyl bromide of step (f) being substituted by 2-pyridylmethyl chloride generated from its hydrochloride immediately before use.

NMR: 0.9(3H,triplet); 1.2–1.3(3H,singlet); 1.4–2.6(4H,complex); 3.4(4H,singlet); 3.5–4.3(6H,complex); 4.6–4.65(4H,singlet); 7.0–7.8(3H,complex); 8.5(1H,broad doublet).

| Elemental Analysis | C | H | N |
|---|---|---|---|
| Calculated for $C_{19}H_{31}O_5N$ | 64.6 | 8.8 | 4.0 |
| Found | 65.5 | 9.3 | 4.0 |

EXAMPLE 18 TO 20

2,2-Dimethyl-3-hydroxy-5-(2-pyridylmethoxymethyl)-5-ethyl oxolane (Isomer A; Isomer B; mixture of isomers A and B)

These compounds were prepared from the compound of Example 17 by a process similar to that described in Example 3, the single isomers being separated from the mixture by column chromatography.

Isomer A (18):

NMR: 0.8(3H,triplet); 1.1–1.2(6H,singlet); 1.3–2.6(4H,complex); 3.45(2H,singlet); 3.65–3.9(1H,complex); 4.7(2H,singlet); 6.9–7.8(3H,complex); 8.5(1H,broad doublet).

| Elemental Analysis | C | H | N |
|---|---|---|---|
| Calculated for $C_{15}H_{23}O_3N$ | 67.9 | 8.7 | 5.3 |
| Found | 67.9 | 9.1 | 5.1 |

Isomer B (19)

NMR: 0.8(3H,triplet); 1.15–1.2(6H,singlet); 1.5–2.6(4H,complex); 3.35(2H,singlet); 4.15(1H,triplet); 4.6(2H,singlet); 6.9–7.8 (3H,complex); 84(1H,broadened doublet).

| Elemental Analysis | C | H | N |
|---|---|---|---|
| Calculated for $C_{15}H_{23}O_3N$ | 67.9 | 8.7 | 5.3 |
| Found | 68.0 | 9.3 | 4.8 |

Mixture of Isomers A and B (20)

NMR: Simple combination of the spectra for 19 and 20.

EXAMPLE 21

2,2-Dimethyl-3-methoxyethyoxymethoxy-5-(2-chlorobenzyloxymethyl)-5-ethyl oxolane This compound was prepared by a method similar to that described in Example 1, substituting 2-chlorobenzyl chloride for the benzyl bromide in step (f).

NMR: 0.8(3H,triplet); 1.2(3H,singlet); 1.3(3H,singlet); 1.35–2.55 (4H,multiplet); 3.35(3H,singlet); 3.4–4.45(7H,multiplet); 4.6 (2H,singlet); 4.7(2H,singlet); 7.0–7.65(4H,multiplet).

| Elemental Analysis | C | H |
|---|---|---|
| Calculated for $C_{20}H_{31}O_5Cl$ | 62.1 | 8.1 |
| Found | 62.2 | 8.3 |

EXAMPLE 22

2,2-Dimethyl-3-hydroxy-5-(2-chlorobenzyloxymethyl)-5-ethyloxolane

This compound was prepared from the compound of Example 21 by a method similar to that described in Example 3.

NMR: 0.85(3H,triplet); 1.15(3H,singlet); 1.25(3H,singlet); 1.35–2.6 (4H,multiplet); 3.4(2H,doublet); 3.5–3.9(1H,multiplet); 4.1 (1H,triplet); 4.65(2H,doublet); 7.0–7.7(4H,multiplet).

| Elemental Analysis | C | H |
|---|---|---|
| Calculated for $C_{16}H_{23}O_3Cl$ | 64.3 | 7.8 |
| Found | 64.4 | 8.2 |

EXAMPLE 23

2,2-Dimethyl-3-methoxyethoxymethoxy-5-(2,6-dichlorobenzyloxymethyl)-5-ethyl oxolane This compound was prepared by a method similar to that described in Example 1, substituting 2,6-dichlorobenzyl chloride for the benzyl bromide in step (f).

NMR: 0.8(3H,triplet); 1.15(3H,singlet); 1.25(3H,singlet); 1.35–2.55 (4H,multiplet); 3.15–4.45(12H,multiplet); 4.70(2H,doublet); 6.75–7.75(3H,multiplet).

| Elemental Analysis | C | H |
|---|---|---|
| Calculated for $C_{20}H_{30}O_5Cl_2$ | 57.0 | 7.2 |
| Found | 56.6 | 7.4 |

EXAMPLE 24

2,2-Dimethyl-3-hydroxy-5-(2,6-dichlorobenzyloxymethyl)-5-ethyl oxolane

This compound was prepared from the compound of Example 23 by a method similar to that described in Example 3.

NMH: 0.8(3H,triplet); 1.1(3H,singlet); 1.2(3H,singlet); 1.25–2.5 (4H,multiplet); 3.35(2H,doublet); 3.5–3.85(1H,broad singlet); 4.0(1H,triplet); 4.75(2H,doublet); 6.65–7.7(3H,multiplet).

| Elemental Analysis | C | H |
|---|---|---|
| Calculated for $C_{16}H_{22}O_3Cl_2$ | 57.7 | 6.7 |
| Found | 55.7 | 6.8 |

EXAMPLE 25

2,2-Dimethyl-4-methoxyethoxymethoxy-5-benzyloxymethyl-5-ethyl oxolane (a) 2.2 g Lithium metal was dissolved in 200 ml of liquid ammonia containing a trace of ferric nitrate, and 21 g (23.5 ml) of ethyl acetate was added. The mixture was stirred for two minutes and 2-formylbut-1-ene (19 g) in diethyl ether (60 ml) was added over 10 minutes at the reflux temperature of the mixture. Stirring was continued for a further 30 minutes, a slight excess of ammonium chloride was added to the reaction mixture and the ammonia was evaporated off. The residue was extracted with diethyl ether, was washed with dilute hydrochloric acid and then with brine, was dried, was evaporated and was distilled at 110°–120° C./10 mm Hg to give 9.2 g (24%) of 2-ethyl-3-hydroxy-4-ethoxycarbonylbut-1-ene (approximately 90% pure).

(b) The product from (a) (9 g) was reacted with methoxyethoxymethyl chloride in a manner similar to that described in step (c) of Example 1. The resulting product was purified on a silica gel column, using 5% acetone in petrol as eluant, to give 10 g of 2-ethyl-3-methoxyethoxymethyl-4-ethoxycarbonylbut-1-ene.

(c) Magnesium (2.36 g) was dissolved in a solution of methyl iodide (6.2 ml) in diethyl ether (120 ml). The product from (b) (9.84 g) in 20 ml diethyl ether was added dropwise and with stirring to the refluxing solution over 20 minutes. A heavy oily precipitate separated out. Saturated ammonium chloride solution was added and the mixture was extracted with diethyl ether, washed with brine, dried over magnesium sulphate and evaporated to give 8.9 g of crude product. The crude product was purified on a silica gel column using 5% acetone in petrol as eluant, to give 7.5 g (80.5%) of 2-ethyl-3-methoxyethyloxymethoxy-5-hydroxy-5-methyl-hex-1-ene.

(d) The product from (c) (7.87 g) was added at 0° C. to m-chloroperoxybenzoic acid (7.15 g of 85% pure material) in methylene chloride (100 ml). The material was stirred for 17 hours, was washed successively with aqueous solutions of sodium sulphite, sodium bicarbonate and sodium chloride, dried and evaporated, yielding 1,2-epoxy-2-ethyl-3-methoxyethoxymethoxy-5-hydroxy-5-methylhexane. This epoxy compound was mixed with m-chlorobenzoic acid in methylene chloride, refluxed for 48 hours and left to stand for a week at ambient temperature. The mixture was then washed successively with aqueous solutions of sodium sulphite, sodium bicarbonate and sodium chloride, dried and evaporated to give 8.2 g of crude product consisting substantially of 2,2-dimethyl-4-methoxyethoxymethoxy-5-hydroxymethyl-5-ethyloxolane.

(e) The product from (d) (2 g) was benzylated in similar manner to that described in step (f) of Example 1. The resulting product was purified on a silica gel column, using 4% acetone in petrol as eluant, to give 1.25 g (50% based on weight of starting material) of the pure desired product.

NMR: 0.9(3H,multiplet); 1.2(6H,multiplet); 1.6(2H,multiplet); 2.1 (2H,multiplet); 3.4(3H,singlet); 3.6(6H,multiplet); 4.3(1H,multiplet); 4.5(2H,singlet); 4.7(2H,singlet); 7.2(5H,singlet).

| Elemental Analysis | C | H |
|---|---|---|
| Calculated for $C_{20}H_{32}O_5$ | 68.15 | 9.15 |
| Found | 67.0 | 9.3 |

EXAMPLE 26

2,2-Dimethyl-4-hydroxy-5-benzyloxymethyl-5-ethyl oxolane

The compound of Example 25 (3.85 g) was added to methanol (50 ml) containing 0.6 ml of 36% hydrochloric acid and the resulting mixture was refluxed for 2½ hours. The mixture was then cooled and the methanol was evaporated to give an oily residue. This residue was dissolved in diethyl ether, washed with brine, dried over magnesium sulphate and evaporated to give 2.64 g (91.7%) of the pure desired product. This product was shown to be pure, and to consist of a mixture of isomers, by thin layer chromatography.

NMR: 0.9(3H,broad triplet); 1.2(6H,multiplet); 1.5(2H,multiplet); 2.0(2H,multiplet); 2.6(1H,broad singlet); 3.3(2H,multiplet); 4.2(1H,multiplet); 4.4(2H,singlet); 7.2(5H,singlet).

| Elemental Analysis | C | H |
|---|---|---|
| Calculated for $C_{16}H_{24}O_3$ | 72.69 | 9.15 |
| Found | 72.4 | 9.5 |

EXAMPLE 27

2,2-Dimethyl-4-oxo-5-benzyloxymethyl-5-ethyl oxolane

The compound of Example 26 (1.2 g), methylene chloride (10 ml) and pyridinium chlorochromate (1.08 g) were stirred together for 24 hours at ambient temperature. The resulting solution was filtered through a column of Fluorosil (Trade Mark) using methylene chloride as eluant. Evaporation of the solvent gave 0.87 g (73.7%) of the desired product.

NMR: 0.8(3H,broad singlet); 1.4(6H,doublet); 1.5(2H,multiplet); 2.4(2H,quadruplet); 3.4(2H,singlet); 4.4(2H,singlet); 7.2(5H,singlet).

| Elemental Analysis | C | H |
|---|---|---|
| Calculated for $C_{16}H_{22}O_3$ | 73.25 | 8.45 |
| Found | 71.7 | 8.7 |

EXAMPLE 28

2,2-Dimethyl-3-methylthiomethoxy-5-benzyloxymethyl-5-ethyl oxolane

This compound was prepared by a method similar to that of Example 9.

NMR: 0.8(3H,triplet); 1.1–1.4(6H,multiplet); 2.2(3H,singlet); 1.4–2.5(4H,multiplet); 3.4(2H,doublet); 3.9–4.4(1H,multiplet); 4.4–5.0(4H,multiplet); 7.4(5H,singlet).

EXAMPLE 29

2,2-Dimethyl-3-anilinocarbonylmethoxy-5-benzyloxymethyl-5-ethyl oxolane

This compound was prepared by a process similar to that of Example 11, the (3-hydroxycarbonylmethoxy)-intermediate being reacted firstly with oxalyl chloride and then with aniline.

NMR: 0.9(3H,triplet); 1.2(6H,singlet); 1.4–2.6(4H,multiplet); 3.4(2H,doublet); 3.6–4.2(3H,multiplet); 4.6(2H,singlet); 7.0–7.8(10H,multiplet); 8.0–8.5(1H,broad singlet).

EXAMPLE 30

Herbicidal Activity

To evaluate their herbicidal activity, compounds according to the invention were tested using as a representative range of plants: maize, *Zea mays* (MZ); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bena, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing, was drenched with a liquid formulation containing a compound of the invention, and in the foliar spray tests the seedling plants were sprayed with such a formulation.

The soil used in the tests was a prepared horticultural loam.

The formulations used in the tests were prepared by diluting with water, solutions of the test compounds in acetone containing 0.4% by weight of an alkylphenol-/ethylene oxide condensate available under the trade name TRITON X-155. The acetone solutions were diluted with water and the resulting formulations applied at dosage levels corresponding to 5 kg and 1 kg of active material per hectare in a volume equivalent to 650 liters per hectare in the soil spray and foliar spray tests, and at a dosage level equivalent to 10 kilograms of active material per hectare in a volume equivalent to approximately 3,000 liters per hectare in the soil drench tests.

In the pre-emergence tests untreated sown soil and in the post emergence tests untreated soil bearing seedlings plants were used as controls.

The herbicidal effects of the test compounds were assessed visually eleven days after spraying the foliage and drenching the soil and twelve days after spraying the soil, and were recorded on a 0–9 scale. A rating 0 indicates growth as untreated control, a rating 9 indicates death. An increase of 1 unit on the linear scale approximately to a 10% increase in the level of effect.

The results of the tests are set out in Table I below.

TABLE I

| Compound of Example No. | Soil Drench 10 kg/ha | | | | | | | | Dosage kg/ha | Foliar Spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 1 | 7 | 6 | 8 | 7 | 3 | 5 | 4 | 4 | 5 | 7 | 6 | 8 | 7 | 6 | 7 | 6 | 7 | 8 | 9 | 9 | 6 | 4 | 4 | 4 | 5 |
| | | | | | | | | | 1 | 6 | 4 | 7 | 4 | 3 | 3 | 0 | 6 | 8 | 8 | 9 | 5 | 4 | 4 | 2 | 3 |
| 2 | 8 | 7 | 9 | 8 | 3 | 2 | 3 | 0 | 5 | 6 | 7 | 7 | 8 | 6 | 4 | 3 | 5 | 7 | — | 9 | 7 | 3 | 0 | 4 | 0 |
| | | | | | | | | | 1 | 4 | 3 | 3 | 6 | 3 | 2 | 0 | 2 | 6 | — | 8 | 6 | 3 | 0 | 0 | 0 |
| 3 | 8 | 7 | 9 | 8 | 4 | 5 | 4 | 2 | 5 | 8 | 6 | 9 | 7 | 7 | 6 | 5 | 6 | 9 | 9 | 9 | 7 | 4 | 2 | 2 | 5 |
| | | | | | | | | | 1 | 0 | 0 | 8 | 0 | 3 | 2 | 2 | 2 | 9 | 8 | 9 | 3 | 2 | 0 | 0 | 0 |
| 4 | 9 | 7 | 9 | 8 | 5 | 4 | 6 | 0 | 5 | 9 | 4 | 9 | 5 | 7 | 6 | 7 | 5 | 9 | 9 | 9 | 7 | 5 | 2 | 3 | 0 |
| | | | | | | | | | 1 | 5 | 0 | 8 | 0 | 1 | 0 | 0 | 1 | 9 | 8 | 9 | 4 | 2 | 0 | 0 | 0 |
| 5 | 7 | 0 | 8 | 0 | 0 | 0 | 0 | 0 | 5 | 2 | 2 | 4 | 0 | 5 | 5 | 4 | 2 | 0 | 0 | 9 | 0 | 0 | 0 | 0 | 0 |
| | | | | | | | | | 1 | 0 | 0 | 0 | 0 | 2 | 2 | 0 | 0 | 0 | 0 | 8 | 0 | 0 | 0 | 0 | 0 |

TABLE I-continued

| Compound of Example No. | Soil Drench 10 kg/ha | | | | | | | | Dosage kg/ha | Foliar Spray | | | | | | | | Pre-emergence | | | | | | | |
|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 6 | 8 | 7 | 9 | 8 | 5 | 3 | 5 | 5 | 5 | 7 | 5 | 9 | 6 | 7 | 6 | 5 | 4 | 9 | 9 | 9 | 8 | 6 | 2 | 3 | 0 |
| | | | | | | | | | 1 | 4 | 0 | 8 | 4 | 2 | 0 | 0 | 1 | 8 | 8 | 9 | 5 | 2 | 0 | 1 | 0 |
| 7 | 8 | 5 | 7 | 7 | 4 | 5 | 6 | 2 | 5 | 6 | 4 | 7 | 7 | 4 | 5 | 4 | 5 | 8 | 4 | 9 | 5 | 2 | 2 | 6 | 3 |
| | | | | | | | | | 1 | 6 | 2 | 7 | 6 | 2 | 2 | 2 | 4 | 7 | 4 | 9 | 3 | 2 | 0 | 3 | 0 |
| 8 | 8 | 6 | 9 | 7 | 0 | 7 | 6 | 6 | 5 | 6 | 2 | 8 | 5 | 3 | 4 | 4 | 6 | 8 | 8 | 9 | 4 | 2 | 4 | 0 | 5 |
| | | | | | | | | | 1 | 5 | 0 | 7 | 0 | 0 | 1 | 0 | 4 | 8 | 3 | 9 | 3 | 0 | 0 | 0 | 0 |
| 9 | 7 | 6 | 9 | 7 | 4 | 3 | 4 | 5 | 5 | 7 | 0 | 8 | 3 | 5 | 5 | 4 | 6 | 7 | 7 | 9 | 8 | 4 | 4 | 0 | 4 |
| | | | | | | | | | 1 | 5 | 0 | 7 | 0 | 4 | 2 | 2 | 4 | 6 | 7 | 8 | 6 | 3 | 2 | 0 | 0 |
| 10 | 8 | 6 | 9 | 7 | 5 | 5 | 3 | 3 | 5 | 7 | 3 | 9 | 7 | 5 | 4 | 4 | 6 | 8 | 4 | 9 | 8 | 4 | 3 | 0 | 5 |
| | | | | | | | | | 1 | 6 | 0 | 8 | 4 | 4 | 2 | 2 | 5 | 7 | 3 | 9 | 6 | 4 | 0 | 0 | 0 |
| 11 | 5 | 5 | 7 | 5 | 0 | 5 | 3 | 2 | 5 | 7 | 4 | 8 | 7 | 5 | 4 | 4 | 5 | 8 | 8 | 9 | 3 | 3 | 0 | 0 | 0 |
| | | | | | | | | | 1 | 6 | 4 | 7 | 5 | 4 | 4 | 4 | 4 | 6 | 8 | 9 | 0 | 3 | 0 | 0 | 0 |
| 12 | 8 | 6 | 9 | 8 | 5 | 6 | 6 | 4 | 5 | 7 | 4 | 9 | 6 | 5 | 4 | 2 | 5 | 9 | 9 | 9 | 7 | 5 | 3 | 4 | 0 |
| | | | | | | | | | 1 | 6 | 2 | 8 | 4 | 3 | 2 | 2 | 3 | 8 | 7 | 9 | 7 | 4 | 2 | 2 | 0 |
| 13 | 4 | 2 | 6 | 0 | 0 | 0 | 0 | 0 | 5 | 5 | 0 | 6 | 4 | 5 | 3 | 4 | 4 | 3 | 0 | 8 | 2 | 0 | 3 | 0 | 0 |
| | | | | | | | | | 1 | 0 | 0 | 2 | 0 | 4 | 0 | 0 | 0 | 0 | 0 | 8 | 0 | 0 | 0 | 0 | 0 |
| 14 | 7 | 6 | 8 | 7 | 3 | 4 | 4 | 6 | 5 | 6 | 2 | 7 | 5 | 4 | 4 | 3 | 5 | 7 | 8 | 9 | 3 | 4 | 3 | 4 | 5 |
| | | | | | | | | | 1 | 5 | 0 | 6 | 3 | 1 | 3 | 2 | 5 | 5 | 6 | 9 | 0 | 3 | 2 | 2 | 0 |
| 15 | 8 | 7 | 8 | 7 | 4 | 5 | 4 | 4 | 5 | 7 | 5 | 8 | 7 | 6 | 6 | 5 | 5 | 8 | 8 | 9 | 5 | 3 | 4 | 5 | 6 |
| 16 | 8 | 7 | 8 | 7 | 3 | 5 | 5 | 2 | 5 | 6 | 5 | 7 | 5 | 4 | 5 | 5 | 6 | 8 | 8 | 9 | 7 | 5 | 5 | 6 | 7 |
| | | | | | | | | | 1 | 4 | 6 | 2 | 2 | 2 | 2 | 4 | 7 | 7 | 8 | 5 | 3 | 3 | 3 | 4 | |
| 17 | 8 | 7 | 7 | 7 | 2 | 3 | 3 | 4 | 5 | 6 | 6 | 7 | 7 | 4 | 4 | 3 | 6 | 9 | 8 | 8 | 8 | 4 | 4 | 5 | 5 |
| | | | | | | | | | 1 | 5 | 6 | 7 | 7 | 1 | 0 | 0 | 4 | 7 | 8 | 8 | 7 | 2 | 1 | 2 | 3 |
| 18 | — | — | — | — | — | — | — | — | — | | | | | | | | | | | | | | | | |
| | | | | | | | | | 1 | 4 | 5 | 5 | 5 | 1 | 2 | 4 | 5 | 6 | 7 | 8 | 6 | 5 | 0 | 4 | 3 |
| 19 | — | — | — | — | — | — | — | — | | | | | | | | | | | | | | | | | |
| 20 | 7 | 7 | 8 | 7 | 3 | 2 | 2 | 2 | 5 | 6 | 5 | 7 | 7 | 2 | 2 | 2 | 5 | 7 | 8 | 8 | 7 | 4 | 0 | 5 | 3 |
| | | | | | | | | | 1 | 4 | 2 | 6 | 2 | 0 | 0 | 0 | 2 | 6 | 5 | 8 | 5 | 3 | 0 | 0 | 0 |
| 21 | 7 | 7 | 7 | 5 | 3 | 5 | 3 | 1 | 5 | 7 | 4 | 7 | 4 | 6 | 6 | 4 | 5 | 8 | 4 | 8 | 3 | 5 | 4 | 4 | 4 |
| | | | | | | | | | 1 | 4 | 0 | 6 | 3 | 3 | 4 | 2 | 3 | 6 | 4 | 8 | 3 | 3 | 2 | 1 | 4 |
| 22 | 7 | 7 | 7 | 7 | 2 | 5 | 4 | 2 | — | | | | | | | | | — | | | | | | | |
| | | | | | | | | | 2 | 4 | 4 | 7 | 4 | 3 | 2 | 3 | 7 | 8 | 9 | 5 | 1 | 2 | 4 | 3 | |
| 23 | 7 | 6 | 6 | 3 | 3 | 5 | 5 | 0 | 5 | 5 | 3 | 7 | 2 | 6 | 6 | 5 | 5 | 6 | 3 | 9 | 3 | 4 | 3 | 2 | 3 |
| | | | | | | | | | 1 | 1 | 0 | 4 | 0 | 5 | 4 | 2 | 4 | 4 | 0 | 8 | 1 | 0 | 2 | 0 | 1 |
| 24 | 7 | 6 | 7 | 7 | 0 | 6 | 4 | 2 | 5 | 5 | 3 | 7 | 5 | 3 | 4 | 4 | 5 | 6 | 5 | 9 | 7 | 0 | 4 | 5 | 5 |
| | | | | | | | | | 1 | 0 | 0 | 7 | 2 | 0 | 2 | 1 | 3 | 5 | 3 | 9 | 4 | 0 | 2 | 4 | 5 |
| 25 | 5 | 0 | 6 | 2 | 2 | 0 | 0 | 0 | 5 | 6 | 2 | 8 | 5 | 3 | 4 | 4 | 6 | 8 | 8 | 9 | 4 | 2 | 4 | 0 | 5 |
| | | | | | | | | | 1 | 5 | 0 | 7 | 0 | 0 | 1 | 0 | 4 | 8 | 3 | 9 | 3 | 0 | 0 | 0 | 0 |
| 26 | 0 | 0 | 0 | 0 | 0 | 0 | 0 | 0 | 5 | 0 | 0 | 2 | 0 | 2 | 5 | 3 | 3 | 0 | 0 | 0 | 0 | 0 | 0 | 0 | 0 |
| 27 | 5 | 0 | 6 | 3 | 4 | 0 | 3 | 3 | 5 | 1 | 0 | 4 | 0 | 4 | 2 | 3 | 5 | 0 | 0 | 8 | 0 | 3 | 2 | 2 | 0 |
| | | | | | | | | | 1 | 0 | 0 | 2 | 0 | 2 | 0 | 0 | 2 | 0 | 0 | 7 | 0 | 3 | 0 | 0 | 0 |
| 28 | 9 | 8 | 9 | 8 | 2 | 5 | 2 | 3 | 5 | 7 | 6 | 9 | 7 | 7 | 7 | 5 | 5 | 9 | 9 | 9 | 8 | 6 | 5 | — | 8 |
| | | | | | | | | | 1 | 6 | 4 | 7 | 7 | 4 | 6 | 4 | 2 | 4 | 9 | 8 | 9 | 7 | 5 | 2 | 4 | 5 |
| 29 | 8 | 7 | 8 | 4 | 0 | 0 | 0 | 0 | — | — | — | — | — | — | — | — | — | — | — | — | — | — | — | — | — |
| | | | | | | | | | 1 | 6 | 7 | 7 | 5 | 6 | 0 | 0 | 3 | 8 | 8 | 9 | 4 | 4 | — | 2 | 0 |

We claim:
1. A tetrahydrofuran derivative of the formula

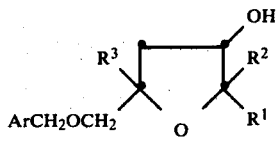

wherein $R^1$ and $R^2$ independently represent a hydrogen atom, a methyl group or an ethyl group, or $R^1$ and $R^2$ together represent a pentamethylene group; $R^3$ represents a methyl, halomethyl, ethyl or methoxymethyl group, and Ar represents phenyl, 2-fluorophenyl, 2-chlorophenyl, 2,6-dichlorophenyl or 2-pyridyl.

2. A compound according to claim 1 wherein $R^1$ and $R^2$ are methyl groups and $R^3$ is an ethyl group.

3. A compound according to claim 2 wherein Ar is a 2-fluorophenyl group.

4. A compound according to claim 2 wherein Ar is a 2-chlorophenyl group.

5. A compound according to claim 2 wherein Ar is a 2,6-dichlorophenyl group.

6. A compound according to claim 2 wherein Ar is a 2-pyridyl group.

7. A herbicidal composition which comprises a herbicidally effective amount of a compound according to claim 1, together with a carrier.

8. A composition according to claim 7, which comprises at least two carriers, at least one of which is a surface-active agent.

9. A method of combating undesired plant growth at a locus, which comprises treating the locus with a herbicidally effective amount of a compound according to claim 1, or a composition thereof.

10. A compound according to claim 2 wherein Ar is phenyl.

* * * * *